United States Patent
Hu (10) Patent No.: US 9,636,172 B2
(45) Date of Patent: May 2, 2017

(54) COMPLIANT BALLOON WITH LIQUID INJECTION

(71) Applicant: MEDTRONIC CRYOCATH LP, Toronto (CA)

(72) Inventor: Yixin Hu, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 141 days.

(21) Appl. No.: 13/906,929

(22) Filed: May 31, 2013

(65) Prior Publication Data

US 2014/0358137 A1    Dec. 4, 2014

(51) Int. Cl.
| | | |
|---|---|---|
| A61B 18/02 | (2006.01) | |
| A61B 18/14 | (2006.01) | |
| A61B 18/04 | (2006.01) | |
| A61B 18/00 | (2006.01) | |
| A61B 90/00 | (2016.01) | |

(52) U.S. Cl.
CPC .......... *A61B 18/1492* (2013.01); *A61B 18/02* (2013.01); *A61B 18/04* (2013.01); *A61B 2018/0022* (2013.01); *A61B 2018/00255* (2013.01); *A61B 2018/00577* (2013.01); *A61B 2018/0212* (2013.01); *A61B 2018/046* (2013.01); *A61B 2090/064* (2016.02)

(58) Field of Classification Search
CPC ..... A61B 18/02; A61B 18/1492; A61B 18/04; A61B 2018/0025; A61B 2018/00255; A61B 2090/064; A61B 2018/0212; A61B 2018/0022

USPC .......................................................... 606/23
See application file for complete search history.

(56) References Cited

U.S. PATENT DOCUMENTS

| | | |
|---|---|---|
| 6,270,493 B1 | 8/2001 | Lalonde et al. |
| 6,575,966 B2 | 6/2003 | Lane et al. |
| 7,300,433 B2 | 11/2007 | Lane et al. |
| 7,527,622 B2 | 5/2009 | Lane et al. |
| 7,648,497 B2 | 1/2010 | Lane et al. |

(Continued)

FOREIGN PATENT DOCUMENTS

| | | |
|---|---|---|
| EP | 1424950 | 6/2004 |
| EP | 1881796 | 1/2008 |

(Continued)

*Primary Examiner* — Joseph Stoklosa
*Assistant Examiner* — Eunhwa Kim
(74) *Attorney, Agent, or Firm* — Christopher & Weisberg, P.A.

(57) ABSTRACT

A system and method for occluding a pulmonary vein. The device includes a treatment device comprising an inner balloon, an outer balloon, and a space therebetween. Delivery of fluid to the inner balloon inflates the treatment element to a first diameter. If a greater treatment element diameter is required to completely occlude a pulmonary vein, fluid is delivered to the space between the first and second balloons, which expands the second balloon and causes the treatment element to have a second diameter that is greater than the first diameter. The fluid delivered to the inner balloon and fluid delivered to the space between the balloons may be from different sources and may be delivered and exhausted independently. Once the treatment element is caused to have a diameter sufficient to completely occlude the pulmonary vein, the treatment element is activated to cool or heat ostial tissue.

25 Claims, 8 Drawing Sheets

(56) References Cited

U.S. PATENT DOCUMENTS

| | | |
|---|---|---|
| 7,727,228 B2 | 6/2010 | Abboud et al. |
| 7,740,627 B2 | 6/2010 | Gammie et al. |
| 7,794,455 B2 | 9/2010 | Abboud et al. |
| 7,871,395 B2 | 1/2011 | Hu et al. |
| 8,298,217 B2 | 10/2012 | Lane et al. |
| 8,382,747 B2 | 2/2013 | Abboud et al. |
| 8,536,667 B2* | 9/2013 | de Graff et al. ............. 257/419 |
| 2002/0007180 A1* | 1/2002 | Wittenberger et al. ......... 606/21 |
| 2004/0243119 A1 | 12/2004 | Lane et al. |
| 2005/0215989 A1 | 9/2005 | Abboud et al. |
| 2006/0030843 A1 | 2/2006 | Lane et al. |
| 2006/0122589 A1* | 6/2006 | Abboud ................ A61B 18/02 606/21 |
| 2007/0032783 A1 | 2/2007 | Abboud et al. |
| 2008/0009925 A1 | 1/2008 | Abboud et al. |
| 2008/0039791 A1 | 2/2008 | Abboud et al. |
| 2008/0091180 A1 | 4/2008 | Abboud et al. |
| 2008/0097421 A1* | 4/2008 | Hu et al. ........................ 606/22 |
| 2008/0103493 A1 | 5/2008 | Abboud et al. |
| 2008/0215043 A1 | 9/2008 | Abboud et al. |
| 2009/0088735 A1 | 4/2009 | Abboud et al. |
| 2009/0182317 A1* | 7/2009 | Bencini ................ A61B 18/02 606/21 |
| 2009/0182318 A1 | 7/2009 | Abboud et al. |
| 2009/0182319 A1 | 7/2009 | Lane et al. |
| 2009/0299356 A1 | 12/2009 | Watson |
| 2010/0042199 A1* | 2/2010 | Burton ........................ 623/1.11 |
| 2010/0114269 A1* | 5/2010 | Wittenberger et al. ........ 607/105 |
| 2011/0184400 A1* | 7/2011 | Pageard ........................ 606/21 |
| 2011/0190751 A1* | 8/2011 | Ingle et al. ..................... 606/21 |
| 2012/0029509 A1* | 2/2012 | Smith ............................ 606/41 |
| 2012/0089047 A1 | 4/2012 | Ryba et al. |
| 2012/0109115 A1 | 5/2012 | Condie et al. |
| 2012/0130359 A1* | 5/2012 | Turovskiy .............. A61B 18/02 606/21 |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136417 A1 | 5/2012 | Buckley et al. |
| 2012/0136418 A1 | 5/2012 | Buckley et al. |
| 2012/0143294 A1 | 6/2012 | Clark et al. |
| 2012/0150267 A1 | 6/2012 | Buckley et al. |
| 2012/0158104 A1 | 6/2012 | Huynh et al. |
| 2012/0245574 A1 | 9/2012 | Lalonde |
| 2012/0253336 A1 | 10/2012 | Littrup et al. |
| 2013/0345688 A1 | 12/2013 | Babkin et al. |

FOREIGN PATENT DOCUMENTS

| | | |
|---|---|---|
| EP | 1980287 | 10/2008 |
| EP | 2387964 | 11/2011 |
| WO | 03020334 | 3/2003 |
| WO | 2005089853 | 9/2005 |
| WO | 2006017073 | 2/2006 |
| WO | 2006118725 | 11/2006 |
| WO | 2008046183 | 4/2008 |
| WO | 2010081221 | 7/2010 |
| WO | 2011091507 | 4/2011 |
| WO | 2012057911 | 5/2012 |
| WO | 2012058156 | 5/2012 |
| WO | 2012058158 | 5/2012 |
| WO | 2012058160 | 5/2012 |
| WO | 2012058167 | 5/2012 |
| WO | 2012019156 | 9/2012 |
| WO | 2012129646 | 10/2012 |

* cited by examiner

COMPLIANT BALLOON WITH LIQUID INJECTION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for treating cardiac conditions such as cardiac arrhythmia. In particular, the present invention relates to a medical device and use thereof, the medical device having an adjustable treatment element.

BACKGROUND OF THE INVENTION

A cardiac arrhythmia is a condition in which the heart's normal rhythm is disrupted. There are many types of cardiac arrhythmias, including supraventricular arrhythmias that begin above the ventricles (such as premature atrial contractions, atrial flutter, accessory pathway tachycardias, atrial fibrillation, and AV nodal reentrant tachycardia), ventricular arrhythmias that begin in the lower chambers of the heart (such as premature ventricular contractions, ventricular tachycardia, ventricular fibrillation, and long QT syndrome), and bradyarrhythmias that involve slow heart rhythms and may arise from disease in the heart's conduction system.

Certain types of cardiac arrhythmias, including ventricular tachycardia and atrial fibrillation, may be treated by ablation (for example, radiofrequency (RF) ablation, cryoablation, hot balloon ablation, ultrasound ablation, laser ablation, microwave ablation, and the like), either endocardially or epicardially. For example, atrial fibrillation (AF) is frequently treated with pulmonary vein ablation (also called pulmonary vein antrum isolation, or PVAI), a procedure that involves positioning a treatment element, such as a cryoballoon or hot balloon (for example, the Toray-Satake balloon), at the mouth or ostium of a pulmonary vein such that the treatment element is in contact with an circumferential area of cardiac tissue at the ostium. After ablation of the ostial tissue, cardiac tissue, such as within or surrounding the pulmonary vein, may be mapped to confirm pulmonary vein isolation. That is, mapping may be used to determine whether aberrant electrical conductivity is still present. For example, a system such as the ARCTIC FRONT® over-the-wire cryoablation catheter system with the ACHIEVE® mapping catheter (both from Medtronic Inc., Minneapolis, Minn.) includes pulmonary vein ablation and mapping functionality.

When a cryoballoon or hot balloon is used as the treatment element in a PVAI procedure, it is desirable that the balloon is in complete contact with the pulmonary vein ostial tissue so as to totally occlude the pulmonary vein. However, ostial sizes can vary greatly, both within the same patient (for example, each of the patient's pulmonary vein ostia may be a different size) and between patients. Currently, a surgeon must have a multitude of differently sized catheters on hand in order to accommodate this variety. Further, a surgeon may have to try several non-reusable catheters to find the right fit, which can be costly and time consuming.

It is therefore desirable to provide a system that includes a treatment element that is adjustable to accommodate any of a variety of ostial sizes.

SUMMARY OF THE INVENTION

The present invention advantageously provides a system, device, and method for treating cardiac conditions such as cardiac arrhythmia. The system may generally include a device having a treatment element having a first balloon defining a chamber and a second balloon disposed about the first balloon, the first balloon and second balloon defining an interstitial space therebetween, a first fluid injection lumen in fluid communication with the chamber and a first fluid reservoir, and a second fluid injection lumen in fluid communication with the interstitial space and a second fluid reservoir. The first balloon may be inflatable to a first diameter by fluid delivered to the chamber from the first fluid reservoir through the first fluid injection lumen and the second balloon being expandable to a second diameter by liquid delivered to the interstitial space by the second fluid reservoir through second fluid injection lumen, the second diameter being greater than the first diameter. The device may further include one or more sensors on the treatment element, such as pressure sensors, and the second diameter may correspond to a diameter of a pulmonary vein ostium within the patient's heart, with the diameter of the pulmonary vein ostium being determined at least in part by signals from the one or more pressure sensors. The second balloon may be substantially compliant and the first balloon may be substantially noncompliant. The device may further include a fluid injection element and/or a heating element disposed within the chamber. The second balloon may have a uniform wall thickness, or it may have one or more portions having a first wall thickness and one or more portions having a second wall thickness.

The device may be used for occluding a pulmonary vein, and may generally include a treatment element including a first balloon defining a chamber and a second balloon disposed about the first balloon, the first balloon and second balloon defining an interstitial space therebetween, a first fluid injection lumen in fluid communication with the chamber, and a second fluid injection lumen in fluid communication with the interstitial space, the first balloon being inflatable to a first diameter by a first fluid delivered to the chamber from the first fluid injection lumen and the second balloon being expandable to a second diameter by a second fluid delivered to the interstitial space by the second fluid injection lumen, the second diameter being greater than the first diameter. For example, the second fluid may be a liquid. The device may further comprise a plurality of pressure sensors on the outer balloon. Further, the second fluid may be at a temperature that causes ablation of tissue.

The method may be used for occluding a pulmonary vein, and may generally include positioning a treatment element in contact with an ostium of the pulmonary vein ostium, the treatment element including a first balloon defining a chamber, a second balloon disposed on the outside of the first balloon, and an interstitial space defined between the first balloon and the second balloon, delivering fluid to the chamber to inflate the first balloon and cause the treatment element to have a first diameter, determining whether the treatment element completely occludes the pulmonary vein ostium, and delivering fluid to the interstitial space to expand the second balloon to cause the treatment element to have a second diameter when it is determined that the pulmonary vein ostium is not completely occluded. The chamber may be in fluid communication with a first fluid injection lumen and a first fluid recovery lumen and the interstitial space is in fluid communication with a second fluid injection lumen and a second fluid recovery lumen. The method may further include, after delivering fluid to the interstitial space to expand the second balloon, determining whether the pulmonary vein is completely occluded, and activating the treatment element when it is determined that the pulmonary vein is completely occluded. Activating the treatment element may include circulating a liquid coolant within the interstitial space, the liquid coolant delivered from the second fluid injection lumen and evacuated by the second fluid recovery lumen. Alternatively, activating the treatment element may include heating a thermal coil within the chamber to increase the temperature of the fluid within the interstitial space and/or delivering a liquid to the interstitial space that is heated to a temperature sufficient to cause ablation of tissue. The treatment element may further include a plurality of pressure sensors on the outer second balloon, the plurality of pressure sensors recording at least one of pressure signals generated by contact between the plurality of pressure sensors and the pulmonary vein and pressure signals generated by a lack of contact between the plurality of pressure sensors and the pulmonary vein. The amount of fluid delivered to the interstitial space to expand the second balloon may be determined at least in part on the pressure signals recorded by the plurality of pressure sensors. Further, fluid may be delivered to the interstitial space in fixed-volume increments.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
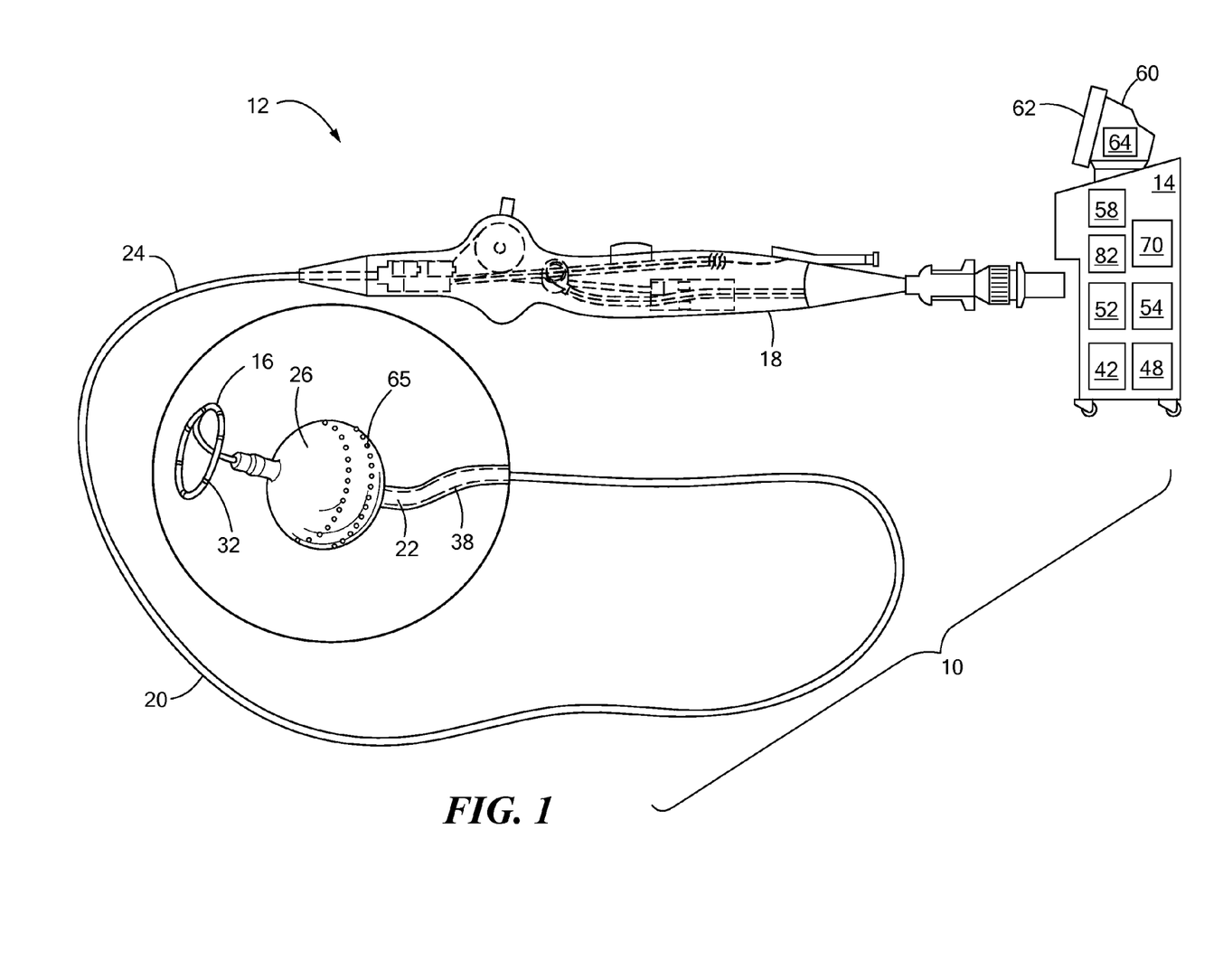
FIG. 1 shows an exemplary system including a medical device having an adjustable treatment element.

Referring now to FIG. 1, a first and second embodiment of a system including a medical device having an adjustable treatment element are shown. The system 10 generally includes a medical device 12 for ablating tissue and a console 14 that houses various system 10 controls. The system 10 may be adapted for cryoablation and/or hot balloon ablation. Additionally or alternatively, the system 10 may be adapted for radiofrequency (RF) ablation and/or phased radiofrequency (PRF) ablation, ultrasound ablation, laser ablation, microwave ablation, or other energy modalities or combinations thereof.

The treatment device 12 may be a catheter having ablation capabilities, and may include mapping capabilities or be usable with a mapping device. As a non-limiting example, the device 12 may be advanceable over a mapping catheter 16. Further, the device 12 may generally include a handle 18, an elongate body 20 having a distal portion 22 and a proximal portion 24, and one or more treatment elements 26 for ablating or thermally treating tissue. For example, the treatment element 26 shown in FIGS. 1-6B include at least an inner balloon and an outer balloon 30. Additionally, the device 12 may include one or more mapping elements for recording electrophysiological signals or may be configured for use with a separate mapping device 16. For example, the device treatment 12 may include one or more lumens through which a mapping device 16 may be disposed (for example, as shown in FIG. 1). The mapping device 16 may be advanced into a pulmonary vein and used to record electrical activity as myocardial cells polarize and depolarize. The treatment device 12 may then be advanced over the mapping device 16 (as in an over-the-wire system) until the treatment element 26 is in contact with the pulmonary vein ostium Alternatively, one or more mapping elements 32 may be disposed on or coupled to the treatment device 12.

Figure 3A:
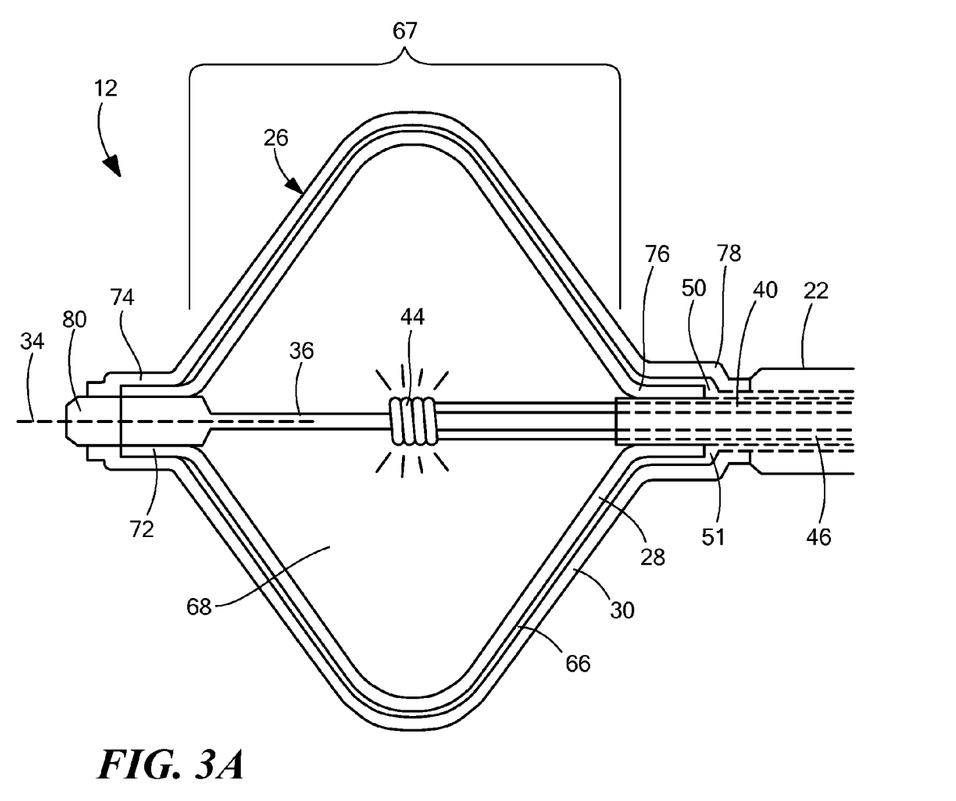
FIG. 3A shows a cross-sectional view of a first embodiment of an adjustable treatment element in a first inflated (treatment) configuration.
Figure 3B:
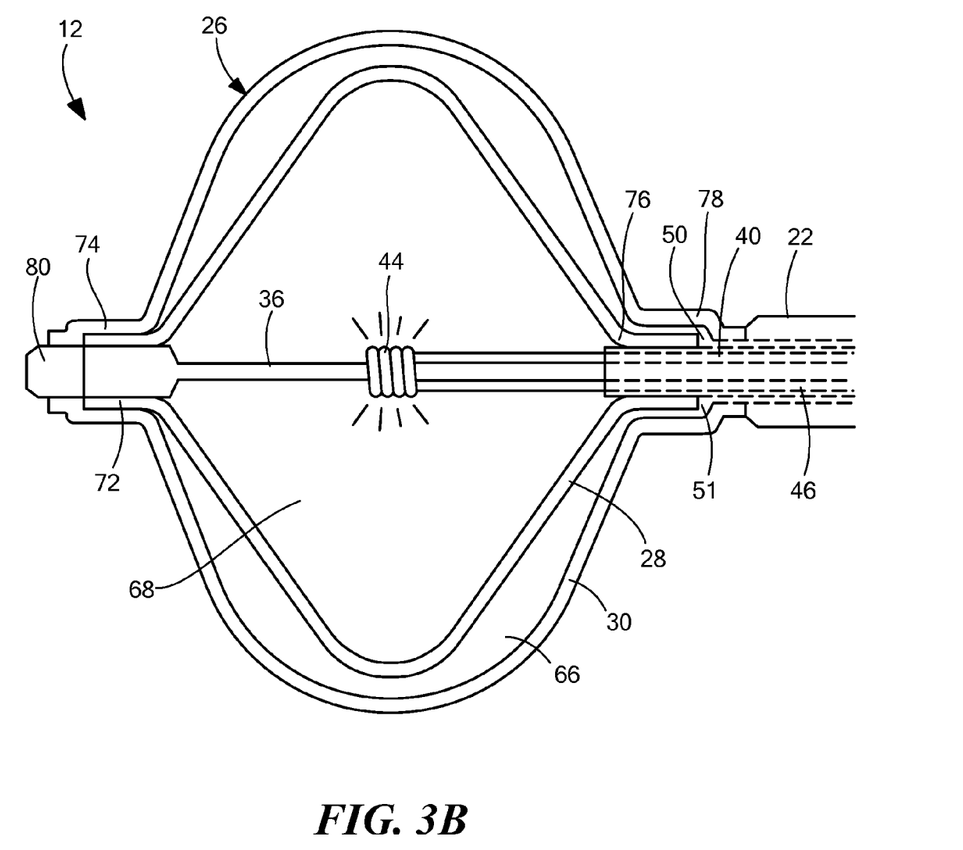
FIG. 3B shows a cross-sectional view of a first embodiment of an adjustable treatment element in a second inflated (treatment) configuration, with fluid injected into the interstitial space between the inner balloon and outer balloon.
Figure 4A:
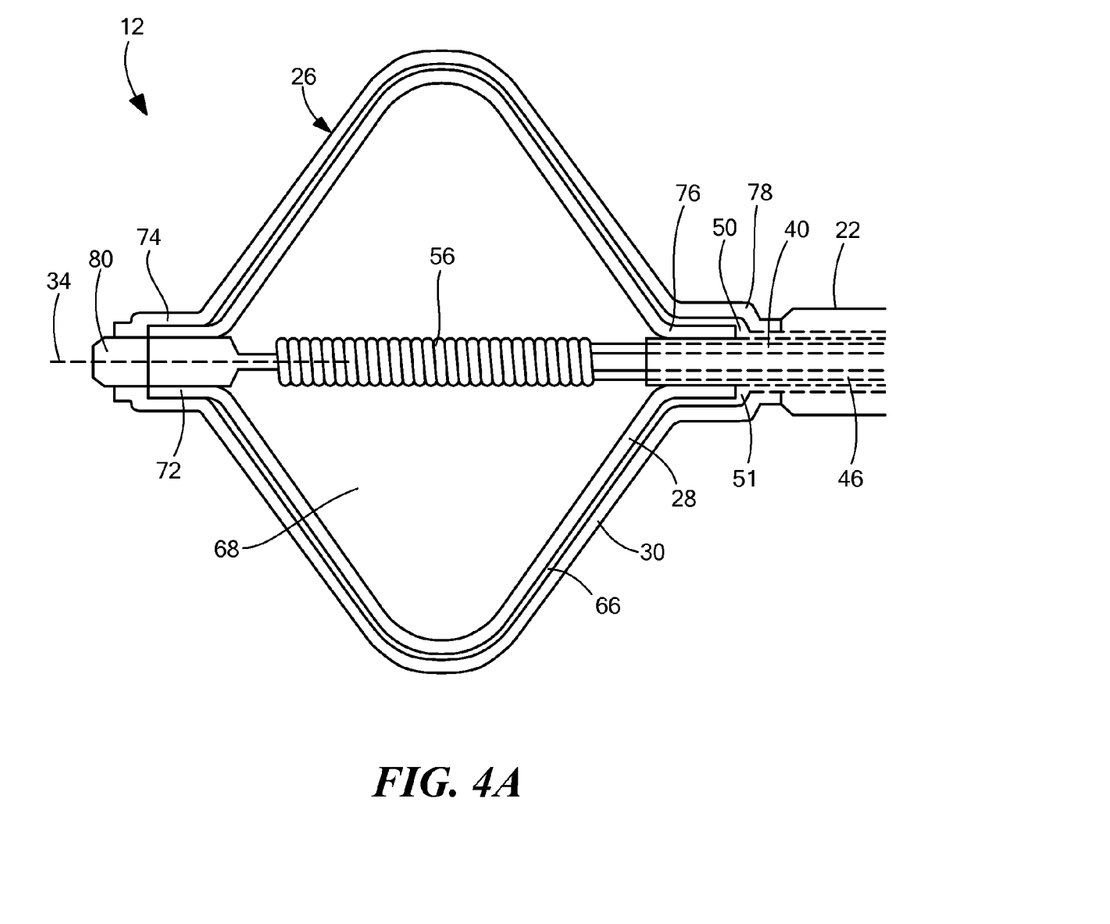
FIG. 4A shows a cross-sectional view of a second embodiment of an adjustable treatment element in a first inflated (treatment) configuration.
Figure 4B:
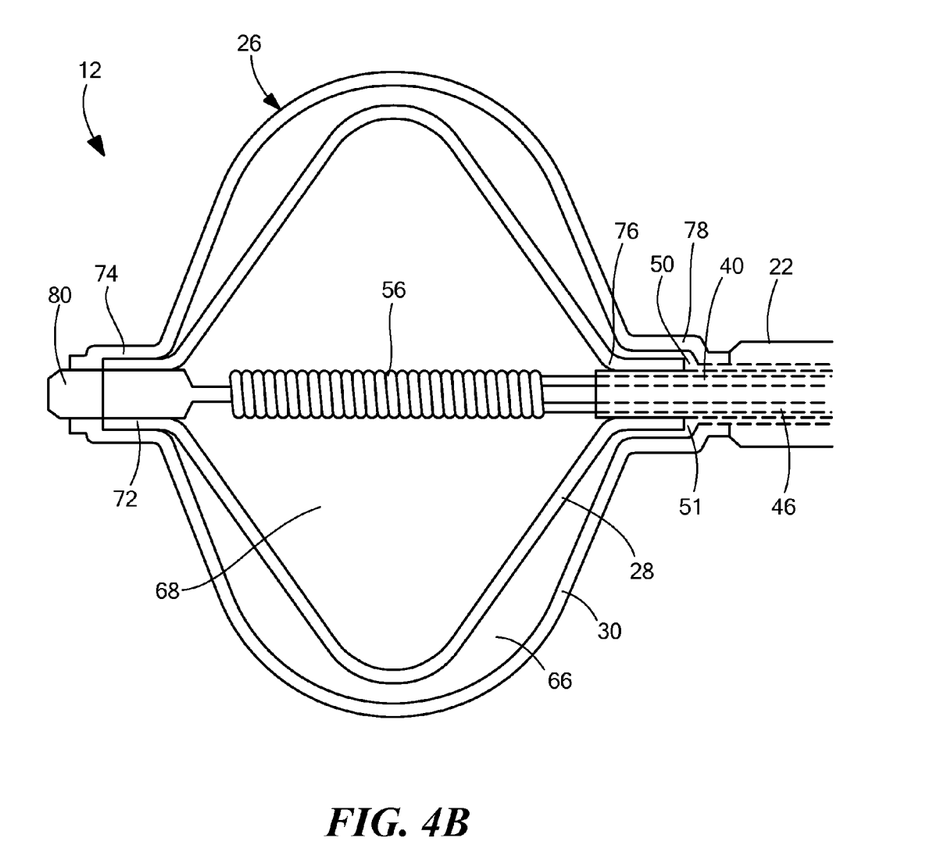
FIG. 4B shows a cross-sectional view of a second embodiment of an adjustable treatment element in a second inflated (treatment) configuration, with fluid injected into the interstitial space between the inner balloon and outer balloon.

The treatment device 12 may have a longitudinal axis 34. Likewise, if a separate mapping device 16 is used, the mapping device 16 may also have a longitudinal axis that is substantially coaxial with the longitudinal axis 34 of the treatment device 12. The one or more treatment elements 26 may be coupled to or disposed on at least a portion of the distal portion 22 of the elongate body 20. For example, the one or more treatment elements 26 (such as a cryoballoon as shown in FIGS. 3A and 3B or a Toray-Satake hot balloon as shown in FIGS. 4A and 4B) may include an inner balloon 28 and an outer balloon 30. As is shown and described in greater detail in the non-limiting examples of FIGS. 3A and 3B, a liquid coolant may be injected into the interstitial space between the first 28 and second 30 balloons when in an inflated configuration to increase the diameter of the treatment element 26.

The treatment device 12 may include a shaft 36 that is disposed within a main lumen 38 of the elongate body 20. In embodiments wherein the shape of the treatment element 26 is adjustable, the shaft 36 may be slidably disposed within the main lumen 38. Further the shaft 36 may define a lumen through which a mapping device 16 may be advanced (for example, as shown in FIG. 1). If the treatment device 12 is a cryoablation catheter (as shown in FIGS. 1, 3A, and 3B), the elongate body 20 may include a main lumen 38, a first fluid injection lumen 40 in fluid communication with a first fluid reservoir 42, a fluid injection element 44, and a first fluid exhaust lumen 46 in fluid communication with a first fluid return reservoir 48. The treatment device 12 may further include a second fluid injection lumen 50 in fluid communication with a second fluid reservoir 52 and a second fluid exhaust lumen 51 in fluid communication with a second fluid return reservoir 54 (as shown in FIGS. 3A and 3B). Alternatively, the second fluid exhaust lumen 51 may be in fluid communication with the first fluid return reservoir 48.

If the treatment device 12 is a hot balloon ablation catheter (as shown in FIGS. 4A and 4B), the elongate body 20 may include a main lumen 38, first fluid injection lumen 40 in fluid communication with a first fluid reservoir 42, a first fluid exhaust lumen 46 in fluid communication with a first fluid return reservoir 48, and a second fluid injection lumen 50 in fluid communication with a second fluid reservoir 52 and a second fluid exhaust lumen 51 in fluid communication with a second fluid return reservoir 54 (as shown in FIGS. 4A and 4B). Alternatively, the second fluid exhaust lumen 51 may be in fluid communication with the first fluid return reservoir 48. Electrical elements (such as a heating or thermal coil 56) within the hot ablation balloon may be in electrical communication with a power source 58 through one or more wires disposed within the main lumen or another lumen of the elongate body 20 (not shown). In some embodiments, one or more other lumens may be disposed within the main lumen, may be disposed within the elongate body 20 along the longitudinal axis 34 parallel to the main lumen 38, and/or the main lumen 38 may function as the fluid injection lumen or the fluid return lumen. If the treatment device 12 additionally includes, for example, electrodes capable of transmitting RF, ultrasound, microwave, electroporation energy, or the like, these elements may also be in electrical communication with one or more power sources 58 via one or more wires disposed within a lumen of the elongate body 20 (not shown).

The console 14 may be in electrical and/or fluid communication with the device 12 and may include one or more fluid (such as coolant, saline, water, or contrast medium) reservoirs 42, 52, fluid return reservoirs 48, 54, power sources 58 (for example, a power source for warming a thermal coil 56 in a hot ablation balloon, or an RF or electroporation energy generator), and one or more computers 60 with displays 62, and may further include various other displays, screens, user input controls, keyboards, buttons, valves, conduits, connectors, power sources, and computers for adjusting and monitoring system 10 parameters. The computer 60 may be in electrical communication with the one or more treatment elements 26 and the one or more recording electrodes 32. Further, the computer 60 may include a processor 64 that includes one or more algorithms executable to evaluate signals received from the one or more mapping elements 32, one or more temperature sensors, pressure sensors, or the like located within or on the treatment device 12 and/or system 10, and to control, monitor, and/or suggest repositioning of the one or more treatment elements 26.

The computer 60 may further be able to determine a fixed volume of fluid for injecting into the interstitial space between the inner balloon 28 and outer balloon 30 when a larger diameter treatment element 26 is required for pulmonary vein occlusion. As a non-limiting example, the computer may be programmable to incrementally inject the fluid until complete occlusion is achieved. Occlusion may be evaluated by using radiography, magnetic resonance imaging, or similar imaging techniques with a contrast medium. The contrast medium may be expelled from the distal portion of the treatment device into the pulmonary vein. If contrast medium is seen leaking into the left atrium of the heart, then the treatment element 26 must be repositioned until complete occlusion is achieved. Once complete occlusion is visually confirmed, no more fluid may be injected between the balloons 28, 30. Additionally or alternatively, the mapping device may form a loop that is in contact with a circumference of the inside of the pulmonary vein. The computer may use this circumference to determine the diameter of the pulmonary vein and a predicted diameter of the ostium. Then, the computer may determine the required volume of fluid that would sufficiently expand the treatment element to occlude the pulmonary vein, and confirm with imaging. Additionally or alternatively, the treatment element 26 may include one or more sensors 65, for example, on the outer surface of the outer balloon 30. As a non-limiting example, the one or more sensors 65 may be discrete sensors distributed around one or more circumferences of the balloon, as shown in FIG. 1. The one or more sensors 65 may be, for example, pressure sensors, force sensors, temperature sensors, impedance sensors, or other sensors useful in assessing contact between the treatment element 26 and tissue. Further, the one or more sensors 65 may send signals to the computer 60 that the computer 60 may use to assess contact between the treatment element 26 and the pulmonary vein ostium. As a non-limiting example, the computer 60 may be programmable to stop the delivery of fluid to the treatment element 26 once signals transmitted by one or more pressure sensors 65 indicate that the treatment element 26 is occluding the pulmonary vein ostium. Again, contact may be visually confirmed using one or more imaging techniques. Other sensors may also be positioned throughout the system to monitor system operation (for example, pressure or temperature sensors). Additional fluid may be added or fluid may be removed from between the balloons 28, 30 as necessary.

Figure 2:
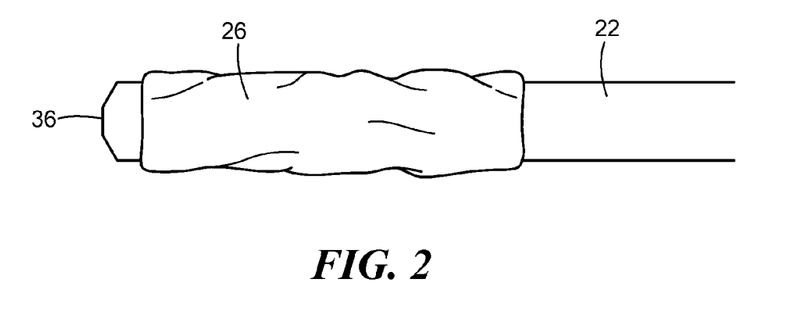
FIG. 2 shows an adjustable treatment element in an uninflated (delivery) configuration.

Referring now to FIG. 2, an adjustable treatment element in an uninflated (delivery) configuration is shown. At least the treatment element 26 and a portion of the elongate body 20 may be passed through the patient's vasculature and into the patient's heart via femoral, brachial, radial, or other access means. The septal wall of the heart may be punctured (for example, by another device or delivery sheath) to allow the treatment element 26 of the device 12 to pass therethrough and access the left atrium. During delivery, the inner and outer balloons 28, 30 of the treatment element 26 may be uninflated and, for example, folded, wound, compressed, or otherwise disposed about the elongate body 20 and shaft 36 in a low-profile manner (as shown in FIG. 2). Once within the left atrium, the inner balloon 28 may be inflated with a treatment fluid, such as a liquid or gas coolant (if, for example, a cryoballoon is used), water, or saline (if, for example, a hot ablation balloon is used). Saline may include a mixture of water and a salt. Further, the treatment element 26 may be fully or partially retracted within a delivery sheath (not shown) during delivery through the patient's vasculature. As used herein, the term "inflate" refers to expansion of the treatment element 26 from a delivery configuration to a treatment configuration (as shown in FIGS. 3A-4B) through the inflation of the inner balloon 28 with a fluid. The outer balloon 30 will also expand along with the inner balloon 28.

Referring now to FIG. 3A, a cross-sectional view of a first embodiment of an adjustable treatment element in a first inflated (treatment) configuration is shown. The treatment element 26 shown in FIGS. 3A and 3B may be configured for use in cryoablation or cryotreatment procedures. The treatment element 26 may include an inner balloon 28 and an outer balloon 30 that have a similar shape, at least when there is no fluid in the interstitial space 66 between the balloons 28, 30. As used herein, the term "interstitial space" may refer to the interface between the inner balloon 28 and outer balloon 30, whether fluid is injected between the inner 28 and outer 30 balloons or not. When fluid is injected between the balloons 28, 30, the interstitial space is increased as the fluid separates the outer balloon 30 from the inner balloon 28. So, in the absence of fluid in the interstitial space 66, the inner 28 and outer 30 balloons may be in contact with each other along the treatment surface 67 (or the area over which the balloons 28, 30 are not affixed to each other, the shaft 36, or the elongate body 20), whereas the balloons 28, 30 may be substantially separated from each other along the treatment surface 67 when fluid is in the interstitial space 66.

The inner balloon 28 may have a fixed shape and outer diameter when inflated, and may be composed of, for example, a noncompliant or low-compliant material such as polyethylene terephthalate (PET) or nylon. Alternatively, the inner balloon 28 may be composed of a shape memory material that expands to an "inflated" shape upon being warmed by the patient's body temperature or using another mechanism to control the shape of the inner balloon 28 (for example, extending the shape memory material to have a small diameter of inner balloon). In this case, the inner balloon may not be in fluid communication with a first fluid injection lumen 40 or a first fluid exhaust lumen 46. Conversely, the outer balloon 30 may be composed of, for example, a compliant or highly compliant material such as polyethylene (PE) or other polyolefins, polyurethanes, or polyvinylchloride (PVC). The compliant nature of the outer balloon 30 may allow it to conform to the shape of the inner balloon 28 when the inner balloon 28 is inflated.

The inner balloon 28 may define a fluid chamber 68 into which a fluid (liquid or gas) may flow to inflate the inner balloon 28. As a non-limiting example, the fluid may be a biocompatible liquid, such as water, saline, contrast medium, or combination thereof. As the outer balloon 30 substantially conforms to the shape of the inner balloon 28 in this configuration, the outer balloon 30 may also be referred to as defining the fluid chamber 68. Although the inner 28 and outer 30 balloons are shown as being separated by a gap in FIG. 3A, this is to illustrate the interstitial space 66 that may later be filled with a liquid coolant. In practice, the inner 28 and outer 30 balloons may be in contact with each other in this configuration, with the interstitial space 66 being defined as fluid is injected between the balloons 28, 30. Fluid may enter the chamber 68 from the injection element 44 through the first fluid injection lumen 40, and may exit the chamber 68 through the fluid exhaust lumen 46. For example, the fluid recover lumen 46 may be in communication with a vacuum source 70.

Each of the balloons 28, 30 may include a distal neck portion 72, 74 and a proximal neck portion 76, 78 that are affixed to the device 12 at a connection point or bond joint. As a non-limiting example, at least part of the distal neck portion 72, 74 of each balloon 28, 30 may be affixed to a distal portion 80 of the shaft 36. Further, an inner surface of the outer balloon distal neck 74 may also be affixed to an outer surface of the inner balloon distal neck 72. Likewise, at least a part of the proximal neck portion 76, 78 of each balloon 28, 30 may be affixed to a distal portion 22 of the elongate body 20. Further, an inner surface of the outer balloon proximal neck 78 may also be affixed to an outer surface of the inner balloon distal neck 76 (as shown in FIG. 3A). However, it will be understood that other balloon attachment means and configurations may be used. If the surgeon determines that the diameter of the balloon in this configuration is sufficient to occlude the pulmonary vein, the treatment procedure may be performed without additional expansion of the outer balloon (that is, without injecting fluid between the inner 28 and outer 30 balloons 30). In that case, the inner balloon 28 may be filled with the fluid coolant. When the procedure is over, the inner balloon 28 may be deflated by removing fluid from the chamber 68. Optionally, removed fluid may be stored, for example, in a fluid return reservoir 48.

Referring now to FIG. 3B, a cross-sectional view of a first embodiment of an adjustable treatment element in a second inflated (treatment) configuration, with fluid injected into the interstitial space between the inner balloon and outer balloon is shown. The fluid may be injected into the interstitial space 66 between the balloons 28, 30 from a second fluid reservoir 52. For example, a volume of fluid determined by the computer 60 may pass from the second fluid reservoir 52 through the second fluid injection lumen 50 into the interstitial space 66. As a non-limiting example, the computer 60 may be programmable to stop the delivery of fluid to the interstitial space 66 once signals transmitted by the one or more pressure sensors 65 indicate that the treatment element 26 is occluding the pulmonary vein ostium. Likewise, fluid may be removed from the interstitial space 66 through the second fluid exhaust lumen 51, which may be in communication with a vacuum source 70. The fluid injected into the interstitial space 66 may be a liquid coolant. The outer balloon 30 may reach temperatures capable of ablating tissue by virtue of the temperature of the liquid in the interstitial space 66. This liquid may be a liquid coolant that is pre-cooled by the console 14 or a liquid (either a liquid coolant or other liquid that is capable of being cooled to ablation temperatures) that is, for example, cooled by virtue of a fluid coolant circulating within the chamber 68 of the inner balloon 28. Alternatively, the liquid within the interstitial space 66 may be cooled by a combination thereof. The computer may determine a fixed volume of liquid coolant to inject, and may inject that amount of fluid into the interstitial space 66 incrementally until complete pulmonary vein occlusion is confirmed. Further, the system 10 may include an adjustment fluid reservoir 82 that is supplied from the second fluid reservoir 52 and one or more valves. As a non-limiting example, a valve between the interstitial space 66 and the adjustment fluid reservoir 82 may be closed while a valve between the second fluid reservoir 52 and the adjustment fluid reservoir 82 is open. This allows the adjustment fluid reservoir 82 to be filled with a fixed amount of fluid before the coolant is allowed to pass into the interstitial space 66. Once the adjustment fluid reservoir 82 is filled with the fixed fluid volume, the valve between the adjustment fluid reservoir 82 and the interstitial space 66 may be opened and the valve between the adjustment fluid reservoir 82 and the second fluid reservoir 52 may be closed.

The outer balloon 30 may have a uniform thickness or may have various thicknesses that determine the shape of the outer balloon 30 and/or maximum outer diameter. For example, the outer balloon 30 may include one or more areas having a first thickness and one or more areas having a second thickness. Depending on the desired outer balloon 30 characteristics, the one or more areas of first and second thicknesses may be positioned partially or entirely around a circumference of the balloon and/or may be discrete areas of various sizes and shapes. This may allow the outer balloon 30 to assume different shapes, depending on the size and/or location of wall thickness differences and the volume of fluid injected into the interstitial space 66.

Referring now to FIGS. 4A and 4B, a cross-sectional view of a second embodiment of an adjustable treatment element in a second inflated (treatment) configuration is shown, both without (FIG. 4A) and with (FIG. 4B) fluid in the interstitial space 66 between the first balloon 28 and second balloon 30. The adjustable treatment element 26 shown in FIGS. 4A and 4B are generally as shown and described in FIGS. 1-3B, except that the treatment element 26 may be usable for hot balloon ablation, such as the Toray-Satake balloon. As such, the inner balloon 28 may include a thermal coil 56 that, when activated, heats fluid within the fluid chamber 68 of the inner balloon 28. Heat from the fluid chamber 68 is transmitted through the first 28 and second 30 balloons to the tissue being treated. Heat from the fluid chamber 68 may warm fluid within the interstitial space 66 to ablation temperatures, or the fluid injected into the interstitial space 66 may be pre-warmed by the system 10 before injection. Like the adjustable treatment element 26 of FIGS. 3A and 3B, the adjustable treatment element 26 of FIGS. 4A and 4B includes first 40 and second 50 fluid injection lumens and first 46 and second 51 fluid exhaust lumens. Fluid, such as a gas or a liquid (for example, water, saline, mixture of water and saline, or other thermally conductive fluids), may be introduced into the fluid chamber 68 from the first fluid injection lumen 40 and removed from the fluid chamber 68 from the first fluid exhaust lumen 46. Likewise, liquid (such as water, saline, contrast medium, or other biocompatible fluids and mixtures thereof) may be injected into the interstitial space 66 between the first 28 and second balloons 30 from the second fluid injection lumen 50 and removed from the interstitial space 66 from the second fluid exhaust lumen 51. For example, fluid may be added and removed from the interstitial lumen 66 for adjusting the outer diameter of the treatment element 26.

Figure 5:
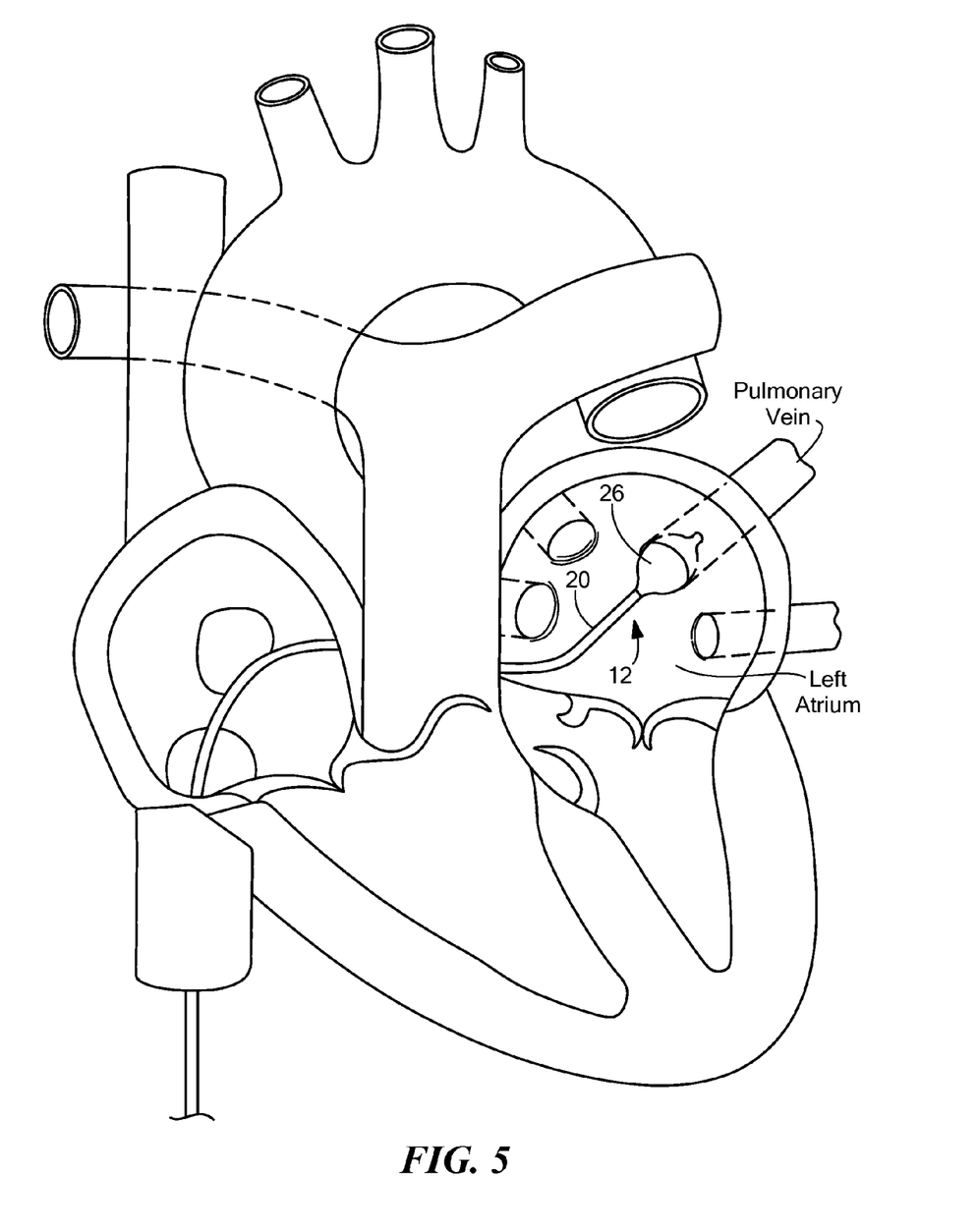
FIG. 5 shows an adjustable treatment element in a first inflated configuration positioned at and occluding a pulmonary vein ostium.
Figure 6A:
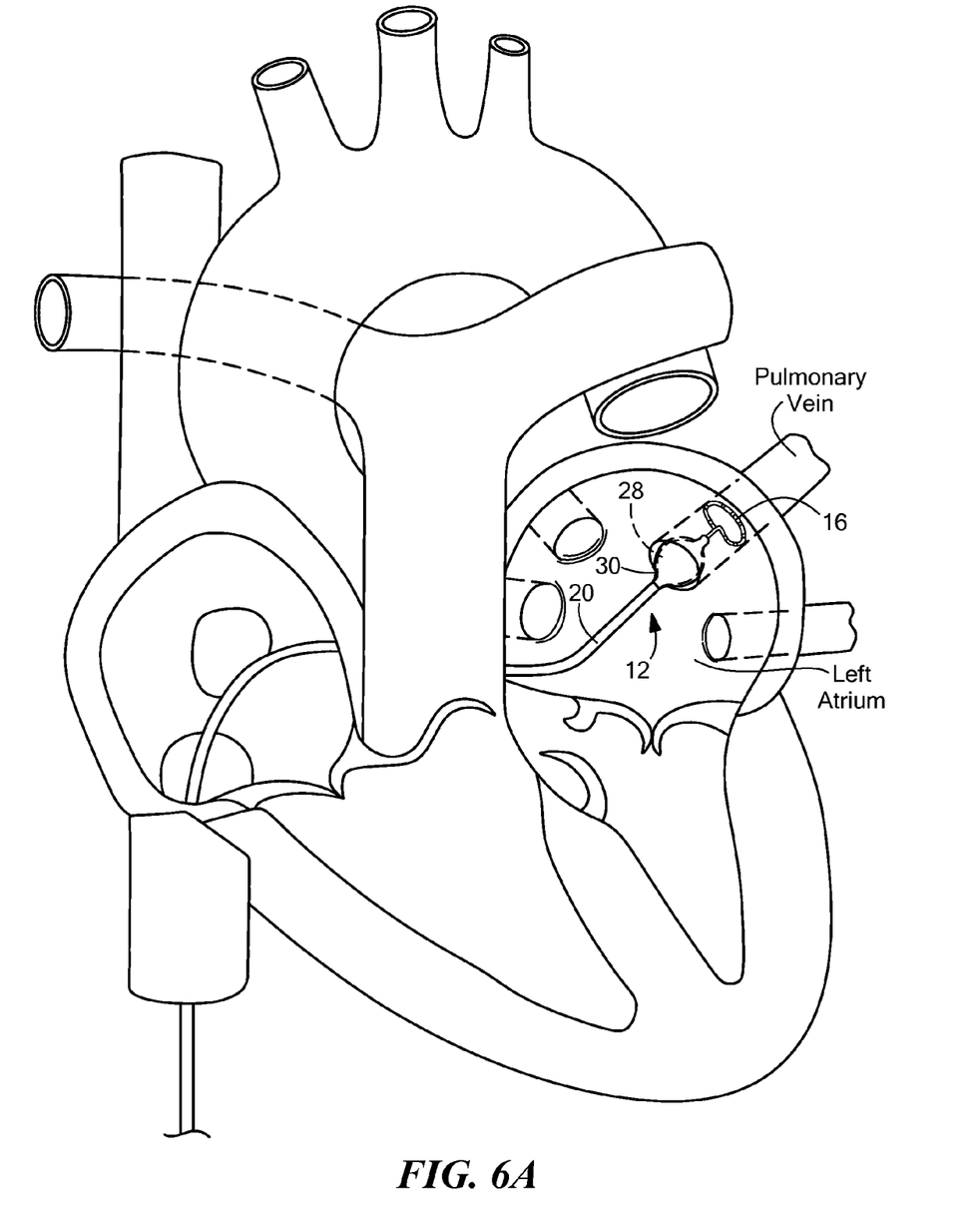
FIG. 6A shows an adjustable treatment element in a first inflated configuration positioned at and failing to occlude a pulmonary vein ostium.
Figure 6B:
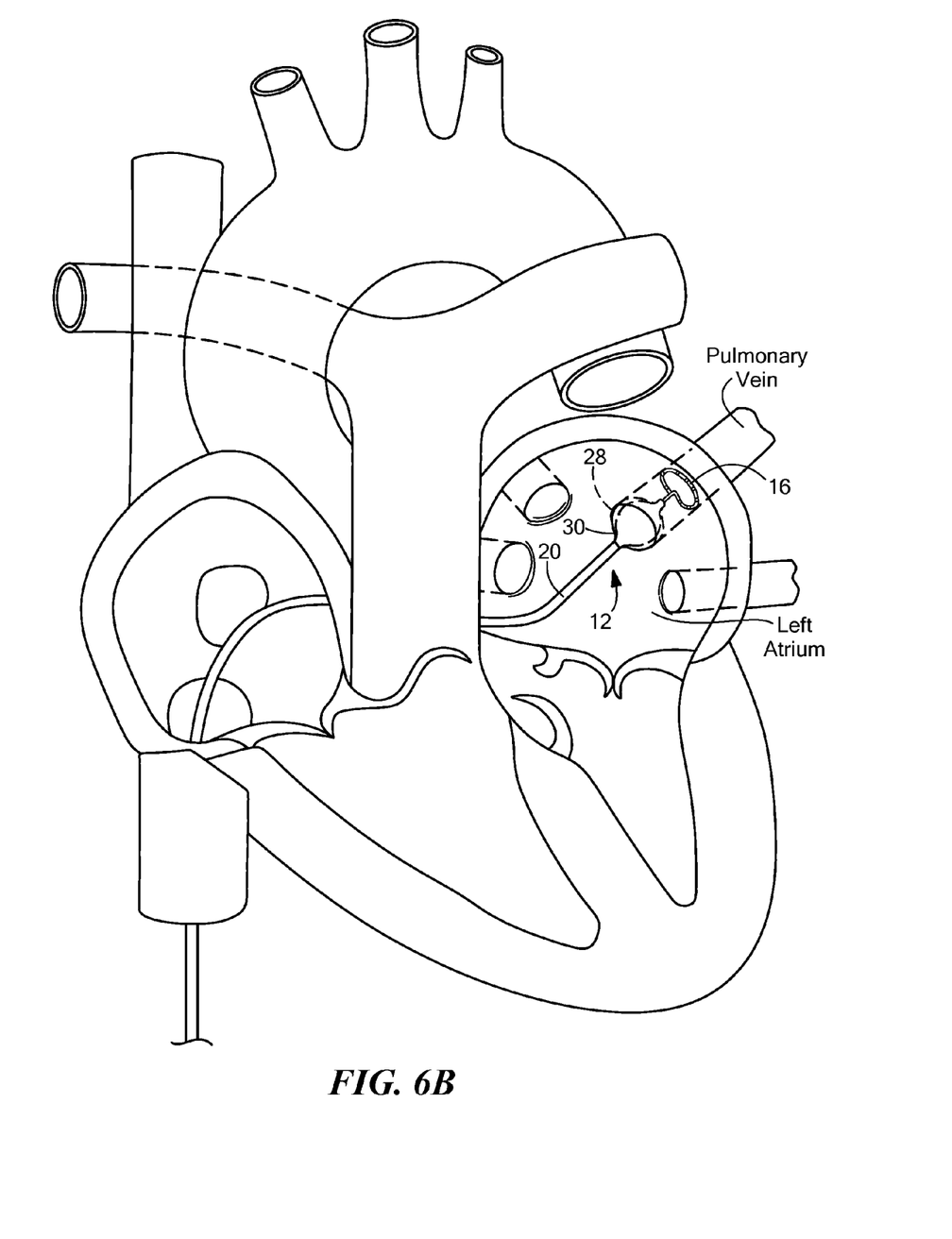
FIG. 6B shows an adjustable treatment element in a second inflated configuration positioned at and occluding the pulmonary vein ostium of FIG. 6A.

Referring now to FIGS. 5-6B, an adjustable treatment element is shown at a pulmonary vein ostium. As shown in FIG. 5, the adjustable treatment element 26 may have a sufficient outer diameter to completely occlude a pulmonary vein ostium when the inner balloon 28 is inflated and no fluid is injected into the interstitial space 66 between the inner 28 and outer 30 balloons. The device 12 is shown in FIG. 5 without a mapping device 16, although it will be understood that one may be used (for example, as shown in FIGS. 6A and 6B). In contrast, FIG. 6A shows a scenario in which the pulmonary vein ostium is wider than the diameter of the adjustable treatment element 26 when the treatment element 26 is inflated but with no interstitial fluid. In this case, the treatment element 26 will not occlude the pulmonary vein. The outer diameter of the treatment element 26 is determined by the maximum inflation volume of the inner balloon 28, as the compliant outer balloon 30 assumes the shape of the inflated inner balloon 28 before fluid is injected into the interstitial space 66. As shown in FIG. 6B, the injection of fluid into the interstitial space 66 may increase the outer diameter of the treatment element 26, allowing the treatment element 26 to completely occlude the pulmonary vein. Fluid may be injected in a single fixed volume or incrementally in fixed volumes. The amount of fluid injected may be determined by the computer 60 (for example, using signals received from one or more pressure sensors 65 to determine contact with the pulmonary vein ostium) and/or determined manually by the user. Complete occlusion may be visually confirmed using one or more imaging techniques. Additionally, fluid may be added or removed (for example, by opening the second fluid exhaust lumen 51 to a vacuum source 70) as required to achieve complete occlusion.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system for treating cardiac arrhythmia within a patient's heart, the system comprising:
a console including:
a first fluid reservoir containing a non-cryogenic inflation fluid;
a second fluid reservoir containing a cryogenic coolant; and
a computer in communication with the first and second fluid reservoirs;
a treatment device including:
an elongate body defining a lumen;
a treatment element coupled to the elongate body having a first balloon and a chamber having a length, and a second balloon coupled to the elongate body and being disposed about the first balloon, the first balloon and the second balloon defining an interstitial space therebetween; and
a first fluid injection lumen in fluid communication with the chamber and the first fluid reservoir, and a second fluid injection lumen in fluid communication with the interstitial space and the second fluid reservoir; and
a mapping device including a plurality of mapping elements and being slidably movable within the treatment device lumen, the mapping device further including a flexible distal end that is configurable into a loop that is in contact with an inner surface of a pulmonary vein such that a diameter of the loop determines an inner diameter of the pulmonary vein, the mapping device being in communication with the computer,
the computer being programmed to:
inflate the first balloon to a first maximum outer diameter at a widest point of the first balloon by the non-cryogenic inflation fluid delivered to the chamber from the first fluid reservoir through the first fluid injection lumen, the first maximum outer diameter being less than an inner diameter of the pulmonary vein;
calculate the inner diameter of the pulmonary vein based on the size of the mapping element loop;
predict a diameter of an ostium of the pulmonary vein based on the calculated inner diameter of the pulmonary vein; and
expand the second balloon to a second maximum outer diameter at a widest point of the second balloon by the cryogenic coolant delivered to the interstitial space by the second fluid reservoir through second fluid injection lumen, the cryogenic coolant within the interstitial space separating the first balloon and the second balloon a distance apart along the entire length of the chamber, the second maximum outer diameter being greater than the first maximum outer diameter, being based on at least one of the calculated inner diameter of the pulmonary vein and the predicted diameter of the ostium of the pulmonary vein, and being sufficient to occlude the pulmonary vein.

2. The medical system of claim 1, wherein the treatment device further includes one or more sensors on the treatment element.

3. The medical system of claim 2, wherein the one or more sensors are pressure sensors.

4. The medical system of claim 3, wherein the second maximum outer diameter corresponds to an inner diameter of a pulmonary vein ostium within the patient's heart, the diameter of the pulmonary vein ostium being determined at least in part by signals from the one or more pressure sensors.

5. The medical system of claim 1, wherein the second balloon is substantially compliant.

6. The medical system of claim 5, wherein the first balloon is substantially noncompliant.

7. The medical system of claim 4, wherein the first balloon is composed of a shape memory material.

8. The medical system of claim 1, wherein the non-cryogenic inflation fluid is selected from the group consisting of: water, contrast medium, saline, and a mixture thereof.

9. The medical system of claim 1, wherein the cryogenic coolant is a liquid.

10. The medical system of claim 1, wherein the treatment device further comprising a fluid injection element disposed within the chamber.

11. The medical system of claim 1, wherein the treatment device further comprising a heating element disposed within the chamber.

12. The medical system of claim 6, wherein the second balloon has a uniform wall thickness.

13. The medical system of claim 6, wherein the second balloon has one or more portions having a first wall thickness and one or more portions having a second wall thickness.

14. A medical system for occluding a pulmonary vein, the medical system comprising:
  a treatment element including a first balloon defining a chamber defining a length and a second balloon being disposed about the first balloon, the first balloon and the second balloon defining an interstitial space therebetween;
  a first fluid injection lumen in fluid communication with the chamber and a second fluid injection lumen in fluid communication with the interstitial space and
  a mapping device extending distally beyond the treatment element, the mapping device including a flexible distal end that is configurable into a loop that is in contact with an inner surface of the pulmonary vein such that a diameter of the loop determines an inner diameter of the pulmonary vein;
  a controller being programmed to:
  inflate the first balloon to a first maximum outer diameter at a widest point of the first balloon by a non-cryogenic inflation fluid delivered to the chamber from the first fluid injection lumen, the first maximum outer diameter being less than an inner diameter of the pulmonary vein,
  expand the second balloon to a second maximum outer diameter at a widest point of the second balloon by a cryogenic coolant delivered to the interstitial space by the second fluid injection lumen, the cryogenic coolant within the interstitial space separating the first balloon and the second balloon a distance apart along the entire length of the chamber, the second maximum outer diameter being greater than the first maximum outer diameter;
  determine the second maximum outer diameter based on the diameter of the loop of the mapping device to sufficiently occlude the pulmonary vein.

15. The medical device of claim 14, wherein the cryogenic coolant is a liquid.

16. The medical device of claim 15, further comprising a plurality of pressure sensors on the second balloon.

17. The medical device of claim 16, wherein the cryogenic coolant is at a temperature that causes ablation of tissue.

18. A method of occluding a pulmonary vein, the method comprising:
  positioning a mapping element including a distal loop within the pulmonary vein such that the distal loop is in contact with an inner circumference of the pulmonary vein, a diameter of the distal loop determining an inner diameter of the pulmonary vein:
  positioning a treatment element in contact with an ostium of the pulmonary vein, the treatment element including a first balloon defining a chamber having a length, a second balloon being disposed outside of the first balloon, and an interstitial space defined between the first and second balloon;
  delivering a non-cryogenic inflation fluid to the chamber to inflate the first balloon and cause the treatment element to have a first maximum outer diameter at a widest segment of the first balloon;
  determining, based on the diameter of the distal loop, a second maximum outer diameter at a widest segment of the second balloon that would completely occlude the ostium of the pulmonary vein; and
  then delivering a cryogenic coolant to the interstitial space to expand the second balloon to cause the treatment element to have the second maximum outer diameter at a widest segment of the second balloon to completely occlude the ostium of the pulmonary vein, the delivery of the cryogenic coolant to the interstitial space expanding the second balloon such that the second maximum outer diameter is greater than the first maximum outer diameter, the cryogenic coolant within the interstitial space separating the first balloon and the second balloon a distance apart along the entire length of the chamber.

19. The method of claim 18, wherein the chamber is in fluid communication with a first fluid injection lumen and a first fluid recovery lumen and the interstitial space is in fluid communication with a second fluid injection lumen and a second fluid recovery lumen.

20. The method of claim 19, further comprising:
  after delivering the cryogenic coolant to the interstitial space to expand the second balloon, determining whether the pulmonary vein is completely occluded; and
  ablating at least a portion of the ostium when it is determined that the pulmonary vein is completely occluded.

21. The method of claim 20, wherein the cryogenic coolant is delivered from the second fluid injection lumen and evacuated by the second fluid recovery lumen.

22. The method of claim 20, wherein the cryogenic coolant within the interstitial space has a temperature sufficient to cause ablation of tissue.

23. The method of claim 18, wherein the treatment element further includes a plurality of pressure sensors on an outer surface of the second balloon, the plurality of pressure sensors recording at least one of pressure signals generated by contact between the plurality of pressure sensors and the pulmonary vein and pressure signals generated by a lack of contact between the plurality of pressure sensors and the pulmonary vein.

24. The method of claim 23, wherein an amount of the cryogenic coolant delivered to the interstitial space to expand the second balloon is determined at least in part on the pressure signals recorded by the plurality of pressure sensors.

25. The method of claim 24, wherein the amount of cryogenic coolant is delivered to the interstitial space in fixed-volume increments.

* * * * *

UNITED STATES PATENT AND TRADEMARK OFFICE
CERTIFICATE OF CORRECTION

PATENT NO. : 9,636,172 B2
APPLICATION NO. : 13/906929
DATED : May 2, 2017
INVENTOR(S) : Yixin Hu Page 1 of 1

It is certified that error appears in the above-identified patent and that said Letters Patent is hereby corrected as shown below:

The FOREIGN PATENTS DOCUMENTS section of the issued patent please replace WO 03020334 3/2003 with the following:

--WO 2003020334 3/2003--

Signed and Sealed this
Eleventh Day of July, 2017

Joseph Matal
*Performing the Functions and Duties of the
Under Secretary of Commerce for Intellectual Property and
Director of the United States Patent and Trademark Office*